United States Patent [19]

Morser et al.

[11] Patent Number: 4,663,146
[45] Date of Patent: May 5, 1987

[54] METHODS AND COMPOSITIONS FOR THE DIAGNOSIS OF BLOODCLOTS USING PLASMINOGEN ACTIVATOR

[75] Inventors: Michael J. Morser; Marc A. Shuman, both of San Francisco, Calif.

[73] Assignee: Codon Genetic Engineering Laboratories, Brisbane, Calif.

[21] Appl. No.: 518,438

[22] Filed: Jul. 29, 1983

[51] Int. Cl.$^4$ .................... A61K 49/00; A61K 43/00
[52] U.S. Cl. ......................... 424/1.1; 424/9; 422/61
[58] Field of Search .......................... 424/1, 9; 422/61

[56] References Cited

U.S. PATENT DOCUMENTS 4,381,346  4/1983  Huasin et al. ................... 424/1.1

OTHER PUBLICATIONS

Camidlo et al., Proc. Soc. Exp. Biol Med., 138 (1971) 277.
Angles-Cano et al., J. Immunol. Methods, 69 (1984) 115–127.

*Primary Examiner*—Christine M. Nucker
*Attorney, Agent, or Firm*—Limbach, Limbach & Sutton

[57] ABSTRACT

Methods for detecting fibrin or fibrin clots in a host suspected of producing fibrin by: introducing labeled tissue plasminogen activator or a binding site fragment derived therefrom into the host's bloodstream and assaying for the presence of concentrations of labeled tissue plasminogen activator in said host. Also provided are kits for practicing the invention.

7 Claims, No Drawings

METHODS AND COMPOSITIONS FOR THE DIAGNOSIS OF BLOODCLOTS USING PLASMINOGEN ACTIVATOR

TECHNICAL FIELD

This invention relates to improved methods and compositions for detecting the presence of a bloodclot in a host by using tissue plasminogen activator.

BACKGROUND ART

The blood of vertebrates is contained within a closed circulatory system. Partially as a means of maintaining this closed system, a mechanism has evolved for sealing this system in the event of injury. One component of vertebrate blood is a kind of cell fragment called a thrombocyte or platelet. Certain dissolved proteins and the platelets are involved in blood-clotting, a complex series of reactions which occur in case of injury to the circulatory system. The end result of these reactions is the formation of a clot, which temporarily seals off the injured area until the damage is repaired.

The main reactions of the clotting process involve thrombokinase, an enzymatically active substance which is released from ruptured platelets. Thrombokinase begins a cascade of events by interacting with both prothrombin (which is inactive) and calcium ions in the blood to produce active thrombin. Thrombin acts on fibrinogen to form fibrin, an insoluable coagulated protein which then forms a meshwork of fibers (a clot) to prevent loss of blood.

However, in many instances, the formation of a clot may be detrimental when it is not repairing an injury. Formation of blood clots within a vessel can block blood flow in that vessel producing damage to the vessel, surrounding tissue, and to tissue served by the vessel. The presence of fibrin within the circulatory system of a host is an indication either of traumatic injury resulting in a lesion to the circulatory system, or pathological condition, having the potential for serious damage.

Currently diagnosis of the presence of blood clots is achieved by cardiovascular imaging techniques using a radio opaque contrast agent administered intravascularly. Current techniques detect clots by demonstrating the alteration of blood flow around a clot or by location of the clot directly. The flow-measuring techniques use a radio opaque contrast agent or colloidal Technetium. The present direct location techniques use $^{125}I$ labeled fibrinogen which must be incorporated into the clot as fibrin. However, this direct technique is not 100% reliable, for example it does not reliably detect old clots. Also, the method is cumbersome to perform, requires 24 hours to provide results, interferes with other diagnostic tests and is ineffective for deep vein thrombosis, a clinically significant diagnostic problem.

In addition, numerous hosts are hypersensitive to the components of contrast agents, their prolonged residence time in the host interferes with other tests and there are numerous contraindications to their use.

As a counter mechanism to clot formation, blood plasma has an enzyme system which dissolves blood clots by catalysis of fibrin to soluble degradation proteins. The enzyme responsible for this transformation, which results in blood clot dissolution, is plasmin. Plasminogen, a precursor of plasmin, is converted to plasmin by enzymes termed plasminogen activators.

The known plasminogen activators include streptokinase, urokinase (u-PA) and a more recently discovered activator, tissue plasminogen activator (t-PA). Urokinase, the plasminogen activator found in urine, is available commercially as a fibrinolytic agent. However, its use has been somewhat limited because of its low specific activity and weak affinity for fibrin.

It has been claimed that a urokinase (u-PA) preparation may be labeled with a radioactive label and used as a diagnostic agent. Hausin, et al., U.S. Pat. No. 4,381,346. However, this use still suffers from many of the inherent defects of u-PA including potential adverse effects noted in u-PA's use as a fibrinolytic drug.

It has been discovered that t-PA has a rather high affinity for fibrin in vitro. Tissue-PA's high affinity for fibrin can be used to provide a diagnostic agent for locating blood clots.

Therefore, it is an object of this invention to provide a diagnostic reagent with high affinity for fibrin.

It is a further object of this invention to provide a diagnostic agent which can be administered systemically without causing adverse reactions.

It is a still further object of this invention to provide a diagnostic agent which will be rapidly cleared from the bloodstream to minimize interference with other diagnostic tests.

It is still a further object of this invention to provide a diagnostic agent to identify blood clots.

DISCLOSURE OF THE INVENTION

This invention provides a method for detecting fibrin or fibrin clots in a host suspected of producing fibrin comprising introducing tissue plasminogen activator which is labeled with a detectable indicator into the host's bloodstream and assaying for the presence of concentration of labeled tissue plasminogen activator in the host.

Another aspect of this invention provides a method for detecting fibrin in a host suspected of producing fibrin comprising introducing a given amount of fibrin binding site fragment of tissue plasminogen activator which is labeled with a detectable indicator into the bloodstream of the host and assaying for the presence of concentration of labeled binding site fragment in the host.

A further aspect of this invention provides diagnostic test kits for the detection of fibrin according to the above methods.

BEST MODE FOR PRACTICING THE INVENTION

Tissue plasminogen activator (t-PA) may be purified from human uterine tissue. Rijken, D. C. et al., Biochem. Biophys. Acta, 580:140–153 (1979). In addition, t-PA can be produced and purified from Bowes Melanoma cells as described by Rijken, D. C., et al., J. Biol. Chem., 256:7035 (1981).

According to recent publications, it may be possible to obtain t-PA by recombinant DNA methods. Pennica, D. et al., Nature, 301:214–221 (1983); Edlund, T. et al., Proc. Nat. Acad. Sci. USA, 80:349–352 (1983).

EXPERIMENTAL

Labeling Tissue Plasminogen Activator

To test for the affinity of labeled t-PA for fibrin, t-PA and u-PA were labeled with $^{125}I$ using the known lactoperoxidase or iodogen techniques. Free iodine was removed by chromatography on Sephadex® G-25 (Pharmacia Fine Chemicals, Uppsala, Sweden). For diagnostic use, t-PA could also be labeled with any known indicator which is detectable in the bloodstream of a host, e.g. $^{131}$I, Selenium, Technetium, or bifunctional chelates. The diagnostic reagent can also be labeled with a non-radioactive indicator detectable by e.g. nuclear magnetic resonance, or other means known in the art. The specific enzyme activity of $^{125}$I labeled t-PA and u-PA were tested and found to be identical to unlabeled material.

Radiolabeled t-PA and u-PA were bound to fibrin monolayers or artificial clots and the amount of enzyme bound to fibrin or free in solution was measured. The results in Table 1 show that t-PA completely binds to fibrin, but not all of the u-PA.

TABLE NO. 1

Comparison in binding affinity between t-PA and u-PA

| Sample | Bound | | Free | |
|---|---|---|---|---|
| | Fibrin | Clot | Fibrin | Clot |
| t-PA | 100% | 100% | 0% | 0% |
| u-PA | 82% | 95% | 17% | 4% |

Labeling of Clots In Vivo

A preparation of $^{125}$I labeled t-PA ($10^5$CPM/unit, $8 \times 10^5$CPM total) in phosphate buffered saline was administered intravenously to a dog. The dog had a clot formed on a catheter which had been introduced into the femoral artery and advanced to the dorsal artery. The samples of blood were withdrawn at intervals and the amount of $^{125}$I was measured. Labeled t-PA was cleared from the system with a half-life of 1.7 minutes.

After 30 minutes the dog was sacrified. Samples of various organs were taken and analyzed. Only three tissues showed significant elevation above the background level of radioactivity in the blood: liver, kidney and the clot. As proteins such as t-PA are cleared through the liver and kidneys, the clot is the only tissue showing specific labeling, due to the affinity of t-PA for fibrin. This labeled the clot with a detectable tracer, in the above example a radioactive tracer, which was visualized and localized using appropriate imaging techniques.

Because of t-PA's high affinity for clots and its fast clearance time it can be used as a diagnostic reagent. Labelled t-PA (using e.g. $^{125}$I or Technetium) can be administered by intraveneous or intraarterial injection in a pharmceutically acceptable carrier. The t-PA circulates throughout the bloodstream and either attaches to the fibrin component of a blood clot or is cleared from the system.

The specificity of the interaction used for the diagnostic imaging can be improved by isolating the fragment of t-PA which binds to fibrin.

Stimulation of Activity by Fibrin Fragment

Enzyme activity of t-PA is enhanced by the presence of fibrin or fragments of fibrin but not by fibrinogen. The enzyme activity was assayed by incubation with plasminogen and a spectrophotometric substrate (HD-val-leu-lys-paranitro-aniline) and the increase in absorbance at A$_{405}$ was measured.

It was shown in this assay that the t-PA activity was increased by the presence of CNBr-derived fragments of fibrin by 80 to 100 fold, but there was no effect on the activity of u-PA. Thus, t-PA not only binds to clots but is stimulated by the presence of a fragment of fibrin not exposed in fibrinogen. The activity of u-PA is not dependent on the presence of this fragment, which is exposed when fibrinogen is converted to fibrin. Therefore, the specificity of u-PA's interaction with fibrin is not as great as the specificity of t-PA.

Tissue-PA was inactivated by treatment with an inhibitor of serine proteases, diisopropyl fluorophosphate (Sigma Chemical Co., St. Louis, Mo.) after labeling with $^{125}$I. This material, although no longer able to activate plasminogen, still bound to fibrin. Thus, the structure responsible for binding to fibrin is not the active site of the enzyme t-PA.

Furthermore, the binding site of t-PA which recognizes fibrin can be separated by fragmentation from the enzymatically active cleavage site. Thus a fragment of t-PA which retains the specific binding affinity for fibrin can be used as a diagnostic which will not display undesirable enzyme activity.

Purification of Binding Site Fragments

Because t-PA specifically binds to fibrin (but not fibrinogen) this property can be used during affinity column chromatography to isolate t-PA from a liquid medium. It has also been found that t-PA will bind to a fragment of fibrinogen prepared by digestion with CNBr.

A chromatography column was prepared by digesting 1.8 grams of fibrinogen in 80 ml of 88% formic acid with approximately 2 grams of CNBr. This mixture was incubated over night at room temperature and an additional 1.5 grams CNBr was added. After eight hours at room temperature 20 ml of distilled H$_2$O was added. This mixture was dialyzed versus 4 liters of distilled H$_2$O with two changes in 72 hours. The digestion fragments were then added to CNBr-activated Sepharose® 4B (cross-linked agarose gel, Pharmacia Fine Chemicals, Uppsala, Sweden) to immobilize them.

The immobilized digestion fragments were poured into a glass column, washed with 5 mM NaPO$_4$ (pH 7.0), 1% Tween®80 (Atlas Chemicals) and a liquid medium containing t-PA was passed through the column. Active t-PA was eluted with 5 mM NaPO$_4$ (pH 7.0), 1% Tween®80 and 0.2M arginine.

The fragment of fibrin containing the site which specifically binds to t-PA and stimulates its activity was isolated by gel filtration on Sephadex® G-100. A 50×900 ml column of Sephadex® G-100 was prepared in a buffer of 10% acetic acid (v/v) and 100 mM NaCl. The fragment material was eluted with the same buffer and the presence of the fragment peak was determined by its ability to enhance t-PA activity. The column peak was pooled and lyophilized then resuspended in 20 ml H$_2$O.

Further purification of this fragment to homogenity was achieved by gel chromatography on Biogel P-60 in a 50×600 ml glass column. The column was prepared in a buffer of 1% (v/v) formic acid in H$_2$O. The fragment was eluted in the same buffer and isolated by determining its ability to enhance t-PA activity. The column peak was pooled and then dialyzed versus 40 liters H$_2$O for 72 hours.

A chromatography column was then prepared by the addition of this purified fragment to CNBr-activated Sepharose® 4B.

Using this column, t-PA labeled with $^{125}$I which had degraded, possibly by autocatalysis, was separated into material which binds t-PA and material which does not.

Material which did not bind t-PA had some proteolytic activity and was lower in molecular weight than t-PA. This material contains the active site but not the fibrin binding site of t-PA.

The bound material could be resolved into two components, one with the molecular weight of t-PA which had enzyme activity and a lower molecular weight component which was inactive. Therefore, a fragment of t-PA was demonstrated which binds the fibrin but has been separated from the fragment carrying the active site.

This labeled binding site fragment can be used in an identical manner in the diagnostic protocol for labeled t-PA.

A similar separation of active site from binding site evidenced above for t-PA has been reported for elastase digestion of plasminogen. The fragment of plasminogen responsible for binding fibrin was shown to consist of two of the structures known as "kringles". Sottrup - Jensen, L. et al., "The Primary Structure of Human Plasminogen" in Progress in Chemical Fibrinolysis and Thrombolysis, Davidson, J. F. et al., eds., 3:191–209, Raven Press, N.Y. (1977).

This "kringle" binding site is a feature found in numerous other compounds, such as plasminogen and prothrombin, which show some specific affinity for fibrin or fibrinogen. Dayhoff, M. O., "Atlas of Protein Sequence and Structure," Nat. Biomedical Research Foundation, Washington, D.C. (1978). Thus, one can expect to fragment these compounds and obtain a binding site for diagnostic applications, e.g. imaging of blood clots, which does not evidence undesirable extraneous activity.

In addition, it is clear that the diagnostic applications of t-PA or of fibrin binding site of t-PA are compatible with therapeutic techniques, so that the application of t-PA can continuously be monitored and modulated according to the amount of labeled t-PA which bypasses a monitored target clot. Thus, for example, in hip surgery it is desirable to dissolve the peripheral clots which form while allowing scar tissue to develop naturally at the surgical site. The application of tissue plasminogen activator can be monitored by imaging downstream from the clot and decreasing the flow of applied t-PA as the imaged t-PA or binding site fragment of t-PA are shown to have saturated the binding availability of the clot.

Although the foregoing invention has been described in some detail by way of illustration and example, for purposes of clarity of understanding, it will be obvious to one skilled in the art that certain changes and modifications may be practiced within the scope of the attended claims.

We claim:

1. A method for detecting fibrin or fibrin clots in a host suspected of producing fibrin comprising:
   introducing a given amount of fibrin binding site fragment of tissue plasminogen activator which is labeled with a detectable indicator into the bloodstream of a host; and
   assaying for the presence of labeled binding site fragment in said host.

2. A method as recited in claim 1 further comprising waiting for the unbound labeled fibrin binding site fragment of tissue plasminogen activator to be cleared from the bloodstream of the host prior to assaying for concentrations of labeled binding site fragment in said host.

3. A method as recited in claim 1 wherein said fibrin binding site fragment of tissue plasminogen activator is labeled with a radioisotope.

4. A method as recited in claim 3 wherein that fibrin binding site fragment of tissue plasminogen activator is labeled with $^{125}$I.

5. A diagnostic kit for the detection and determination of fibrin or fibrin clots in a host suspected of producing fibrin, comprising:
   a given amount of fibrin binding site fragment of tissue plasminogen activator which is labeled with a detectable indicator;
   a pharmaceutically acceptable carrier suitable for injection into the blood stream of the host, which labeled fragment and carrier are packaged as a unit.

6. A diagnostic kit as recited in claim 5 wherein said labeled fibrin binding site fragment of tissue plasminogen activator is labeled with a radioisotope.

7. A diagnostic kit as recited in claim 6 wherein said radioisotope is $^{125}$I.

* * * * *